US011162133B2

United States Patent
Zhang et al.

(10) Patent No.: US 11,162,133 B2
(45) Date of Patent: Nov. 2, 2021

(54) DETECTION OF AN AMPLIFICATION PRODUCT USING PH-SENSITIVE DYE

(71) Applicant: New England Biolabs, Inc., Ipswich, MA (US)

(72) Inventors: Yinhua Zhang, North Reading, MA (US); Nathan Tanner, Peabody, MA (US); Thomas C. Evans, Jr., Topsfield, MA (US)

(73) Assignee: New England Biolabs, Inc., Ipswich, MA (US)

( * ) Notice: Subject to any disclaimer, the term of this patent is extended or adjusted under 35 U.S.C. 154(b) by 395 days.

(21) Appl. No.: 16/306,319

(22) PCT Filed: May 12, 2017

(86) PCT No.: PCT/US2017/032405
§ 371 (c)(1),
(2) Date: Nov. 30, 2018

(87) PCT Pub. No.: WO2017/209920
PCT Pub. Date: Dec. 7, 2017

(65) Prior Publication Data
US 2019/0169683 A1 Jun. 6, 2019

Related U.S. Application Data

(60) Provisional application No. 62/345,429, filed on Jun. 3, 2016.

(51) Int. Cl.
*C12Q 1/68* (2018.01)
*C12Q 1/6844* (2018.01)
(Continued)

(52) U.S. Cl.
CPC ...... *C12Q 1/6846* (2013.01); *C12Q 1/6816* (2013.01); *C12Q 1/6876* (2013.01);
(Continued)

(58) Field of Classification Search
CPC .................................................... C12Q 1/68
(Continued)

(56) References Cited

U.S. PATENT DOCUMENTS 10,253,357 B2 * 4/2019 Mitra .................. C12Q 1/6846
10,724,091 B1 * 7/2020 Meagher ............. C12Q 1/6876
(Continued)

FOREIGN PATENT DOCUMENTS

WO 2015/033229 A2 3/2015
WO 2015/164770 A1 10/2015
WO WO-2015164770 A1 * 10/2015 ........... C12Q 1/6844

OTHER PUBLICATIONS

Gill, et al., Nucleosides Nucleotides Nucleic Acids. 27: 224-243 (2008).
(Continued)

*Primary Examiner* — Aaron A Priest
(74) *Attorney, Agent, or Firm* — New England Biolabs, Inc; Harriet M. Strimpel

(57) ABSTRACT

Methods are provided for a rapid, low cost approach to monitoring an amplification reaction. This includes monitoring the progress of isothermal or PCR amplification reactions to completion using pH-sensitive dyes that are either colored or fluorescent. Compositions are described that include a mixture of a DNA polymerase, deoxyribonucleotide triphosphate and Tris buffer in the range of 1.5 mM Tris to 5 mM Tris or equivalent.

7 Claims, 2 Drawing Sheets

Specification includes a Sequence Listing.

(51) Int. Cl.
     *C12Q 1/6816*      (2018.01)
     *C12Q 1/6876*      (2018.01)
     *G01N 33/52*       (2006.01)

(52) U.S. Cl.
     CPC ....... *G01N 33/52* (2013.01); *C12Q 2527/119* (2013.01); *C12Q 2527/125* (2013.01); *C12Q 2545/114* (2013.01); *C12Q 2563/173* (2013.01); *C12Y 207/07007* (2013.01)

(58) Field of Classification Search
     USPC ........................................................ 435/6.1
     See application file for complete search history.

(56) References Cited

U.S. PATENT DOCUMENTS

| | | | |
|---|---|---|---|
| 2014/0057268 A1* | 2/2014 | Tanner | C12Q 1/6844 |
| | | | 435/6.12 |
| 2017/0023555 A1* | 1/2017 | Ou | C12Q 1/6813 |
| 2017/0247668 A1* | 8/2017 | Kim | C12N 1/20 |
| 2019/0060895 A1* | 2/2019 | Myers, III | B01L 7/52 |
| 2019/0083975 A1* | 3/2019 | Mitra | C12Q 1/6844 |

OTHER PUBLICATIONS

Kim, et al, Bioanalysis, 3:227-39 (2011).
Nagamine, et al., Mol. Cel. Probes, 16:223-9 (2002).
Notomi, et al., Nucleic Acids Res., 28:E63 (2000).
Nagamine, et al., Clin. Chem., 47:1742-3 (2001).

* cited by examiner

SEQUENCE LISTING

<160> NUMBER OF SEQ ID NOS: 6

<210> SEQ ID NO 1
<211> LENGTH: 42
<212> TYPE: DNA
<213> ORGANISM: Enterobacteria phage lambda

<400> SEQUENCE: 1
cgaactgttt cgggattgca ttctggaact ccaaccatcg ca        42

<210> SEQ ID NO 2
<211> LENGTH: 43

```
<212> TYPE: DNA
<213> ORGANISM: Enterobacteria phage lambda

<400> SEQUENCE: 2
ggagcctgca taacggtttc gtcgactcaa tgctcttacc tgt            43

<210> SEQ ID NO 3
<211> LENGTH: 21
<212> TYPE: DNA
<213> ORGANISM: Enterobacteria phage lambda

<400> SEQUENCE: 3
gttggtcact tcgacgtatc g                                    21

<210> SEQ ID NO 4
<211> LENGTH: 20
<212> TYPE: DNA
<213> ORGANISM: Enterobacteria phage lambda

<400> SEQUENCE: 4
gctcgccgac tcttcacgat                                      20

<210> SEQ ID NO 5
<211> LENGTH: 18
<212> TYPE: DNA
<213> ORGANISM: Enterobacteria phage lambda

<400> SEQUENCE: 5
tttgcagacc tctctgcc                                        18

<210> SEQ ID NO 6
<211> LENGTH: 20
<212> TYPE: DNA
<213> ORGANISM: Enterobacteria phage lambda

<400> SEQUENCE: 6
ggatttttta tatctgcaca                                      20
```

DETECTION OF AN AMPLIFICATION PRODUCT USING PH-SENSITIVE DYE

BACKGROUND

Nucleic acid amplification has become an essential tool in life sciences fields, from basic laboratory research to clinical diagnostics. The use of diagnostic nucleic acid amplification has expanded outside of specialized laboratory settings as improvements in cost and amplification techniques have enabled wider access. The key technique for amplification has long been the polymerase chain reaction (PCR), which, although widely used and understood, requires thermal cycling equipment and some mechanism of amplification detection, either through real-time monitoring (e.g., fluorimetry) or post-reaction electrophoresis. Sequence-specific isothermal amplification represents a promising alternative that obviates the need for even basic equipment; examples of this approach include strand displacement amplification (SDA), helicase dependent amplification (HDA), and loop-mediated isothermal amplification (LAMP).

LAMP in particular has been used in a number of field and point-of-care diagnostics. LAMP reactions use a strand-displacing DNA polymerase (and reverse transcriptase for RNA targets) with four to six primers, resulting in highly exponential amplification. This high degree of DNA synthesis can facilitate visual detection of positive amplification based on the precipitation of magnesium pyrophosphate. This detection can be performed in real time with a specialized turbidity instrument or by direct visual assessment, although the latter typically requires a long incubation time (≥60 minutes), and the precipitate can be difficult to see under even ideal conditions.

Alternative detection methods for nucleic acid amplification use the color change of a metal-sensitive indicator, such as a shift from dark yellow to yellow (calcein), dark blue to blue (hydroxynaphthol blue), or dark blue to light blue (malachite green).

The calcein and hydroxynaphthol blue color shifts are difficult to discern by eye. Furthermore, calcein requires inclusion of the ionic form of manganese, which can inhibit polymerase reactions. Malachite green features an additional color change in the negative reactions, with a change from dark blue to clear. These indicators require long incubation times (typically 60 minutes) and have been demonstrated with only moderate sensitivity (>100-1000 copies of target). Metal-sensitive indicators have been successfully applied in LAMP reactions; however, the concentrations of reaction cofactors and degree of amplification required have so far precluded extension to PCR and other methods. Intercalating nucleic acid dyes can be added to the reactions for real-time and visual detection, but clear visualization requires UV illumination.

Point-of-care and field diagnostics require rapid and simple tests, ideally detecting target nucleic acid in less than 30 minutes and without sophisticated and costly equipment. New diagnostic methods are therefore needed.

SUMMARY

In general, in one aspect, a method is provided for performing an amplification reaction. In some embodiments, the method may comprise: setting up a buffered amplification reaction that comprises 1.5 mM to 5 mM Tris or equivalent thereof (the lower end of the range may be 1 mM Tris or less for embodiments of the methods and compositions of amplification reaction mix). The buffered amplification reaction additionally comprises a pH sensitive dye; and the method includes incubating the amplification reaction under amplification conditions; and, after or during the incubation, detecting a change in color of the amplification reaction, wherein a change in color of the reaction indicates that an amplification product has been produced.

In some embodiments, the amplification conditions may be isothermal conditions. For example, in some embodiments, the amplification may be done by LAMP, HDA, SDA, a recombinase polymerase amplification (RPA), rolling circle amplification (RCA), signal mediated amplification of RNA technology (SMART), single primer isothermal amplification (SPIA), nucleic acid sequence based amplification (NASBA) or a nicking enzyme amplification reaction (NEAR).

In other embodiments, the amplification conditions may include thermocycling (e.g., may be PCR).

In some embodiments, the change in color of the amplification reaction may be visible by eye. As such, the detecting step may be done by a naked eye.

In some embodiments, the change in color of the amplification reaction may be compared to a control reaction in which no template has been added.

In some embodiments, the amplification may have a starting pH in the range of pH 7-8.5.

In some embodiments, the amplification reaction may comprise a biological sample.

In some embodiments, the method may provide a diagnostic for infectious disease.

In some embodiments, the pH sensitive dye is soluble. For example, in some embodiments, the pH sensitive dye may be a colored, water soluble dye that is detectable in visible light.

In some embodiments, the dye may be selected from cresol red, phenol red, m-cresol purple, bromocresol purple, neutral red, thymol blue, and naphtholphthalein, although other dyes may be used.

In general, in one aspect, an aqueous amplification reaction mix is provided that includes: a polymerase, 1.5 mM to 5 mM Tris or an equivalent thereof, a single pH sensitive dye, dNTP, one or more primers; and one or more templates wherein the reaction mix changes color only during amplification reaction.

In some embodiments, the aqueous amplification reaction mix may have a pH in the range of pH 7-8.5.

In some embodiments, the single pH sensitive dye is soluble.

In some embodiments, the soluble pH sensitive dye is a colored dye detectable in visible light.

In some embodiments, the dye is selected from cresol red, phenol red, m-cresol purple, bromocresol purple, neutral red, naphtholphthalein, and thymol blue.

BRIEF DESCRIPTION OF THE FIGURES

The invention may be understood from the following detailed description when read in conjunction with the accompanying drawings. It is emphasized that, according to common practice, the various features of the drawings are not to scale. Indeed, the dimensions of the various features are arbitrarily expanded or reduced for clarity. Included in the drawings are the following figures.

DESCRIPTION OF EMBODIMENTS

Figure 1:
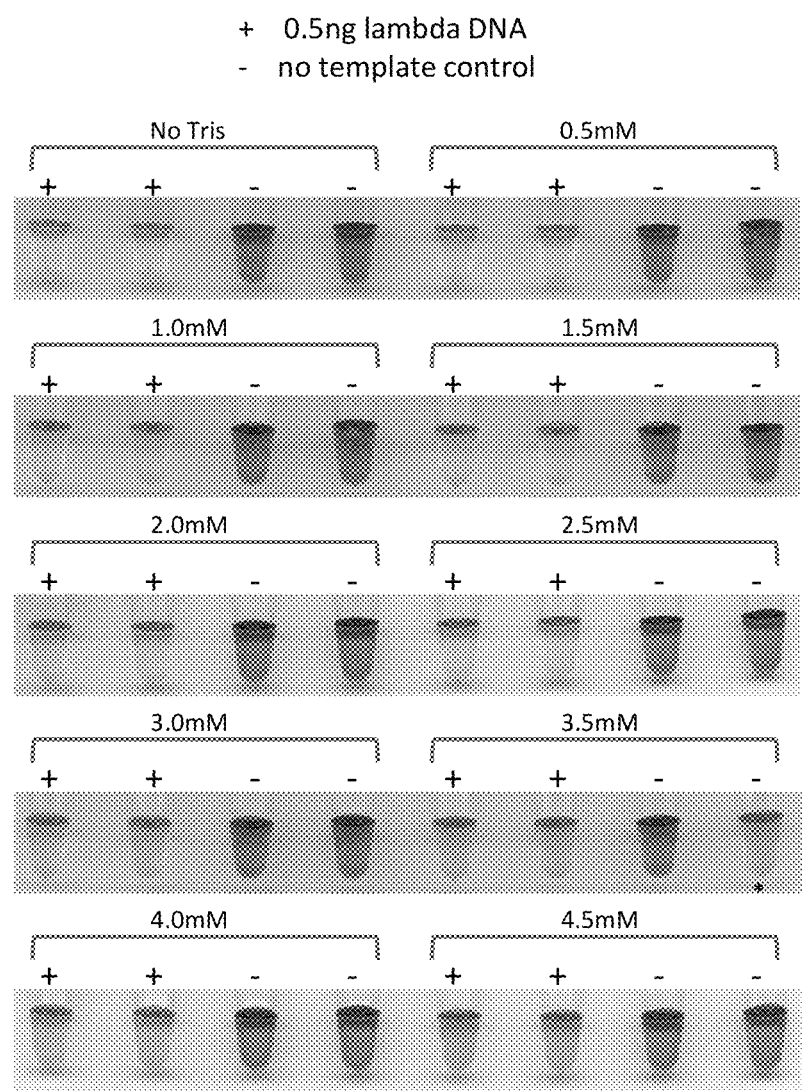
FIG. 1 shows that buffered amplification reactions contain a pH-sensitive dye change color when an amplification product is produced. In this example, LAMP was used to amplify a target amplicon from lambda phage in buffers that contain Tris at various concentrations (0-4.5 mM Tris). In all conditions tested, a color change occurred in the presence of template, indicating that presence of the DNA amplification lowers the pH by an amount that is sufficient to change the color of the dye. In the absence of the template, there is no DNA synthesis and there is no color change except a tube that is likely contaminated by aerosol carryover amplicon pollutant which nevertheless indicates active LAMP reaction leads to color change.

Described herein is a method for detecting a product in a buffered amplification reaction. The method uses one or more pH sensitive dyes where the color of the dye(s) changes as the reaction progresses. A change in the color of the reaction indicates that an amplification product has been produced. Here one or more pH sensitive dyes change color in response to a change in pH that occurs during amplification. This is different from the prior art which uses dyes solely to monitor the combination of reagents prior to an amplification reaction and utilizes a plurality of dyes where the combination of dyes is the cause of the observed color change and ensures that a reaction mixture has been properly combined as determined by the color change. Where the term "a pH sensitive dye" is used, this refers to one or more pH sensitive dyes.

The change in color of a dye in response to a pH change that occurs during nucleic acid amplification in the presence of 1.5 mM-5 mM Tris is surprising. It would not be expected that that pH of the reaction would change significantly during the course of the reaction (e.g., from pH of about 8.0 to a pH of about 6.0), much less that the pH of the reaction would change by an amount that would be sufficient to change the color of a pH sensitive dye. In U.S. Pat. No. 9,034,606, color change was described at buffer concentrations below 1 mM Tris. In embodiments of the method, change in color of pH sensitive dyes resulting from amplification is observed in any buffer at a concentration equivalent to 1.5 mM to 5 mM Tris such as 2 mM, 2.5 mM, 3 mM, 3.5 mM, 4 mM, 4.5 mM or 5 mM Tris or any other concentration in the specified range. A person of ordinary skill in the art will be acquainted with Tris buffer and equivalent buffers that are standard within the art such as Tricine, Bicine, TAPS, MOBS, and Hepes (Sigma Aldrich, St. Louis, Mo.) including DIPSO, TAPSO, HEPPSO, POPSO, TEA, EPPS, HEPBS, AMPD and TABS (Sigma Aldrich, St. Louis, Mo.).

Without wishing to be bound to any particular theory, when a DNA polymerase incorporates a deoxynucleoside triphosphate into the nascent DNA, the released by-products include a pyrophosphate moiety and a proton (a hydrogen ion). The release of protons results in a change in pH of the reaction and, while the reaction is buffered, the amount of protons released as a by-product of the reaction may overwhelm the buffering agent, and lower the pH by an amount that is sufficient to change the color of the dye.

Typical amplification reactions contain primers (e.g., one, two, four or six primers), sample (which may or may not contain template to which the primers bind), nucleotides (corresponding to G, A, T and C), a buffering agent (1 mM to 5 mM Tris or 1.5 mM to 5 mM Tris or an equivalent buffer thereof), one or more salts (e.g., $(NH_4)_2SO_4$, NaCl, $MgSO_4$, $MgCl_2$, etc.), a bacterial or archaebacterial polymerase (which may or may not be thermostable and may or may not have strand displacing activity), and any necessary cofactors and optional detergents, etc. Examples of thermostable polymerases that can be used in a PCR or polymerases for use in isothermal amplification reactions include, but are not limited to Taq, Tfi, Tzi, Tth, Pwo, Pfu, Q5®, Phusion®, OneTaq®, Vent®, DeepVent®, Klenow(exo-), Bst 2.0 and Bst 3.0 (New England Biolabs, Ipswich, Mass.), PyroPhage® (Lucigen, Middleton, Wis.), Tin DNA polymerase, GspSSD LF DNA polymerase, Rsp (OptiGene, Horsham, UK) and phi29 polymerase, etc.

The method may, in general, be employed to detect reaction products in an amplification reaction in which an amplicon, i.e., an amplification product, is produced. Such reactions include, but are not limited to, PCRs, linear polymerase reactions, NASBAs, RCAs, isothermal amplification reactions, etc. In some embodiments, the method may comprise incubating the amplification reaction under isothermal conditions, in which case the products may be amplified by transcription mediated amplification (TMA), nucleic acid sequence-based amplification, SMART, SDA, RCA, LAMP, isothermal multiple displacement amplification (IMDA), HDA, SPIA, circular helicase dependent amplification (SHDA), recombinase polymerase amplification (RPA) and NEAR. These methods are generally described in Gill, et al 2008 (Nucleosides Nucleotides Nucleic Acids. 27: 224-243, (2008); Kim, et al, Bioanalysis, 3:227-39 (2011); Nagamine et al., Mol. Cel. Probes, 16:223-9 (2002); Notomi et al., Nucleic Acids Res., 28:E63 (2000); and Nagamine et al., *Clin. Chem.*, 47:1742-3 (2001), among others. In other embodiments, the method may comprise thermocycling the amplification reaction. In these embodiments, the products may be amplified by PCR, which term includes reverse transcriptase PCR (RT-PCR) and inverse PCR.

The detection may be qualitative or quantitative. In some embodiments, for example, the method may comprise simply detecting whether there has been a change in the color during the amplification reaction, thereby indicating the presence or absence of an amplification product. In some embodiments, the color of the reaction may be compared to a color chart or the color of one or more controls, e.g., an amplification reaction that does not contain any template and/or an amplification reaction that contains a different template that is amplified in the amplification reaction, thereby allowing a user to determine if the reaction contains a product or not. In other embodiments, for example, the method may comprise quantifying the change in the color of the amplification reaction, thereby indicating the amount of product in the amplification product. In some embodiments, the color of the reaction may be compared to a color chart or the color of one or more controls, e.g., amplification reactions that contain varying amounts of a different template that is amplified in the amplification reaction, thereby allowing a user to quantify the amount of product and/or template in the amplification reaction. In some cases, the color of the reaction may be read within 1 hour, e.g., 5 minutes -50 minutes, after the reaction starts.

The pH-sensitive dye used may be selected according to any characteristic, e.g., their color change (i.e., whether they change from violet to yellow, red to yellow, or yellow to red, etc.), the initial pH of the amplification reaction (e.g., whether the reaction initially has a pH of greater than pH 8.0, a pH of 7.5-8.5, or a pH of 6.5-7.5, etc., and whether the color change is going to be detected using a machine (e.g., a colorimeter, fluorimeter or spectrophotometer) by human eye (i.e., without the aid of a colorimeter, fluorimeter or spectrophotometer). The selected dye generally changes color in a pH range at which the polymerase is operational (e.g., a pH of 5-10).

There are a wide range of pH-sensitive dyes that can be used in the present method. Examples of pH sensitive dyes that change color at different pHs are described below. These examples are not intended to be limiting. Suitable visible dyes include: neutral red, which has a clear-yellow color when the pH is higher than 8 and a red color when the pH is less than 6.8; phenol red, which has a red color when the pH is higher than 8 and a yellow color when the pH is less than 6.4; cresol red, which has a reddish-purple color when the pH is higher than 8.8 and a yellow color when the pH is less than 7.2; thymol blue, which has a blue color when the pH is higher than 9.6 and a yellow color when the pH is less than 8.0; phenolphthalein, which has a fuchsia color when the pH is higher than 10 and colorless when the pH is less than 8.3; and naphtholphthalein, which has a greenish color when the pH is higher than 8.7 and a pale-reddish color when the pH is less than 7.3. The properties of some of the dyes that can be used in the method are summarized in Table 1. The term "visual" includes those dyes that can be detected by the "naked eye" where the "naked eye" refers to visualization without instrumentation. The "naked eye" includes the use of contact lenses and/or spectacles. The contact lenses/spectacles may include lenses and/or tinting to enhance or eliminate certain wavelengths of light.

| Indicator | High pH Color | pH Transition | Low pH Color |
| --- | --- | --- | --- |
| Bromocresol purple | Violet | 6.5-5.2 | Yellow |
| Neutral red | Clear-yellow | 8.0-6.8 | Red |
| Phenol red | Red | 8.2-6.8 | Yellow |
| Cresol red | Red | 8.8-7.2 | Yellow |
| Naptholphthalein | Blue | 8.8-7.3 | Clear-red |
| m-Cresol purple | Violet | 9.0-7.4 | Yellow |
| Thymol blue | Blue | 9.6-8.0 | Yellow |
| Phenolphthalein | Red | 10-8.0 | Red |

Other examples of pH indicators include:, methyl yellow, methyl orange, bromophenol blue, naphthyl red, bromocresol green, methyl red, azolitmin, nile blue, thymolphthalein, alizarin yellow, salicyl yellow, nitramine. The color may transition outside the range of traditional DNA polymerase tolerances, but the principle of amplification detection may be applied to alternate detection methods with an indicator appropriate for desired pH range.

pH-sensitive fluorescent dyes can be detected using a fluorometer. Like visual dyes mentioned above, pH-sensitive fluorescence dyes have different levels of fluorescence emission or a shift of peak emission wavelength at different pH. Both the change in brightness and the shift in peak absorption can be easily detected using systems that are equipped with proper filter sets. Fluorescent dyes for use in embodiments of the invention include 5-(and-6) carboxy SNARF-1 which features a shift in fluorescence based on pH. At high pH (pH 9) SNARF-1 maximum absorbance/emission at $A_{max}$ 575 nm/$Em_{max}$ 650 nm. These values blue-shift significantly when the pH lowers, to $A_{max}$ 525/$Em_{max}$ 590. This fluorescence shift allows simultaneous monitoring of the two states of the dye, with one fluorescence channel matching the high pH form (shows fluorescence decrease with amplification) and another channel the low pH form (fluorescence increase). We measured a 90% loss of fluorescence for the high pH form (measured in ROX channel of CFX96 instrument (Bio-Rad, Hercules, Calif.) or 200% gain of fluorescence (HEX channel) upon pH drop from pH 10 to pH 6 calibration solution. Other suitable fluorescent dyes related to SNARF-1 have been developed for monitoring pH change, including SNARF-4F and SNARF-5F, SNAFRs, SNAFL, 5-(and-6)-carboxynaphthofluorescein, 6-JOE, Oregon Green® (Life Technologies, Grand Island, N.Y.). Other fluorescent pH indicators include 2',7'-bis-(2-carboxyethyl)-5-(and-6)-carboxyfluorescein, acetoxymethyl ester (BCECF-AM) (Life Technologies, Grand Island, N.Y.) which at pH 9 has a absorbance/emission profile of $A_{max}$ 500 nm/$Em_{max}$535 nm. It also features a spectral blueshift as pH drops, but the low pH form is much less efficient in excitation, and the effective readout is limited to the decrease in fluorescence from the high pH form. An approximately 80% reduction in fluorescence was measured for BCECF-AM (FAM channel of CFX96) from pH 10 to pH 6. BCECF is derived from fluorescein and a number of dyes related to fluorescein show similar sensitivity to pH change.

Visual and fluorescent dyes including those mentioned above can be chemically modified to have altered colorimetric properties in response to pH changes. These modification can create dyes that are either brighter or change color at a narrower pH range and thus allow a better detection.

There are many applications of the above-described DNA amplification detection method. For example, in some embodiments, the method can be used as a means to indicate successful amplification reactions in standard molecular biology protocols, obviating the need for gel electrophoresis. This detection can include indication of the presence or absence of desired DNA species, as in screening colonies for carrying a correct insert in a plasmid. Detection of species extends to diagnostic applications, as the presence or absence of specific DNA or RNA target species can be indicated by color change after cycling or incubation time. This is particularly suited to isothermal amplification methods such as LAMP in field or point-of-care testing. The rapidity and robustness of the color change enable efficient detection of diagnostic targets quickly without sophisticated equipment. Color or fluorescence change can be monitored in real time, allowing quantification of amount of target nucleic acid where such information is required, e.g. sequencing library preparation, transcription profiling, and load measurement.

Embodiments of the invention provide a simple, robust, rapid, sensitive and cost effective means for visual detection of nucleic acid amplification.

All references cited herein are incorporated by reference.

EXAMPLES

Unless otherwise indicated, LAMP reactions contained, 50 mM KCl, 8 mM $MgSO_4$, 1.4 mM dNTPs, Tris (0 to 4.5 mM, pH8.0) and 0.1% v/v Tween-20 and were incubated at 65° C. All components were mixed in water, and 1 M KOH was used to adjust the pH to 8.0, as measured by a pH meter.

Reactions were performed using a primer set for amplifying an amplicon from lambda phage DNA. Reactions were incubated for 30-60 minutes at 65° C. with either 50 µM or 100 µM of a phenol red in the presence or absence of template (lambda phage DNA). Immediately before the reactions, primers (e.g., Lambda FIP: CGAACTGTTTCGG GATTGCATTCTGGAACTCCAACCATCGCA (SEQ ID NO:1); Lambda BIP: GGAGCCTGCAT- AACGGTTTCGTCGACTCAATGCTCTTACCTGT (SEQ ID NO:2); Lambda F3: GTTGGTCACTTCGACGTATCG (SEQ ID NO:3); Lambda B3: GCTCGCCGACTCTTCACGAT (SEQ ID NO:4); Lambda LoopF: TTTGCAGACCTCTCTGCC (SEQ ID NO:5) and Lambda LoopB: GGATTTTTTATATCTGCACA (SEQ ID NO:6)) were added at the following concentrations: 1.6 µM FIP/BIP, 0.2 µM F3/B3, and 0.4 µM LoopF/B. Template DNA was 0.5 ng lambda DNA (New England Biolabs, Ipswich, Mass.), or 10 pg-100 ng HeLa genomic DNA (New England Biolabs, Ipswich, Mass.). Bst DNA polymerase, Large Fragment or Bst 2.0 DNA polymerase (New England Biolabs, Ipswich, Mass.) at 0.32 U/µL was used.

The dyes used are obtained from Sigma-Aldrich (St. Louis, Mo.) and made into a 50 mM stock in water, diluted to 2.5 mM (25×) in water, and pH adjusted above the indication threshold. Dye was added to the reaction mixture and visually inspected to check initial pH, and an image was recorded using a photo scanner. Reactions were incubated at 65° C. for the indicated time, visually inspected for color change after removal from reaction temperature, and scanned.

Example 1

Detection of LAMP Amplification Using a pH-Sensitive Visual Dye

To determine the level of tolerance to Tris buffering, colorimetric LAMP assays were performed in reactions with increasing level of Tris (0 to 4.5 mM, pH 8.0). The pH of the reactions before incubation was the same by Tris and measured to be pH 7.95-8.01. The starting color of these reactions was the same and was bright pink in all of them. After LAMP reaction at 65° C. for 40 minutes, reactions turned yellow when target DNA was added or remained bright pink when there was no target DNA. The degree of color change was more pronounced with 2.0 mM Tris than at 4.5 mM. Nevertheless, even in the presence of 4.5 mM Tris in the LAMP reaction, the color change caused by LAMP amplification is evident and easy to differentiate with the naked eye. These results are shown in FIG. 1.

Example 2

Various Primer Sets can be Used for Colorimetric LAMP

Figure 2:
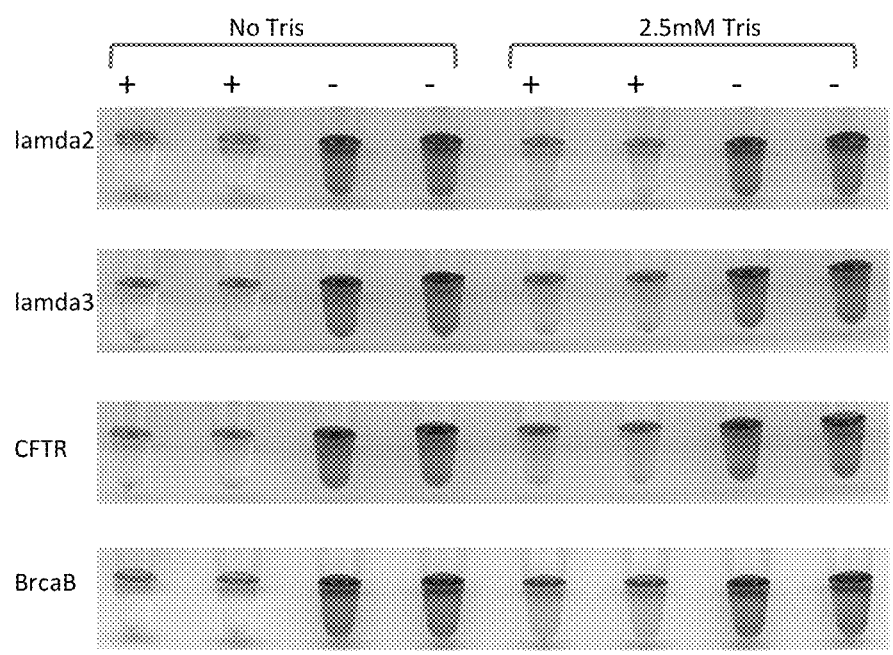
FIG. 2 shows that the color change observed in FIG. 1 is consistent for a variety of different amplicons that are amplified in buffers containing 2.5 mM Tris. Here lambda 2, Lambda 3, CFTR and BRCA-B are shown. Lambda1 and Lambda3 amplify two different fragments of the Lambda DNA. CFTR and BRCA-B amplify regions of the CFTR and BRCA gene from the human genome.

LAMP reactions were performed containing no or 2.5 mM Tris with primer sets for amplification of a first amplicon from lambda (lambda2), a second amplicon from lambda DNA (lambda3), an amplicon of the CFTR gene and an amplicon from the BrcaB gene from the human genomic DNA. The results showed that colorimetric detection based on pH performed well with this level of Tris buffering regardless of primer set. These results are shown in FIG. 2.

Example 3

Detection of RT-LAMP Amplification Using a pH-Sensitive Visual Dye

For RT-LAMP, identical conditions can be used with the addition of 0.3 U/µL RTx™ reverse transcriptase (New England Biolabs, Ipswich, Mass.) and an RNA template as substrate. All solutions of primers, dNTPs, and template DNAs can be prepared in water to minimize buffer carryover. All reactions can be repeated at least once and can be performed in duplicate. A pH-sensitive dye is included at 100 mM.

Example 4

Detection of PCR Amplification Using a pH-Sensitive Visual Dye

PCR can be performed in a 50 L reaction containing 50 mM KCl, 2 mM $MgCl_2$, 0.3 mM dNTPs, and 0.075 U/µL Taq DNA polymerase (New England Biolabs), Tris (0 to 4.5 mM) with pH adjusted to ~8.5 with 1 M KOH. Reactions are incubated at 95° C. for 2 minutes followed by 40 cycles of 95° C. for 10 seconds, 58° C. for 15 seconds, and 68° C. for 30 seconds. Amplification is detected using 100 mM phenol red and confirmed with 1% agarose gel electrophoresis.

Example 5

Detection of SDA Amplification Using a pH-Sensitive Visual Dye

SDA can be performed in a solution containing 10 mM $(NH_4)_2SO_4$, 50 mM KCl, 8 mM $MgSO_4$, 0.4 mM dATP/dGTP/dTTP, and 0.8 mM 2'-deoxycytidine-5'-O-(1-thiotriphosphate) (dCTP-αS; Trilink Biotechnologies, San Diego, Calif.), Tris (0 to 4.5 mM), with the pH adjusted to ~8.5 with 1 M KOH. Reactions contain 0.5 M each of forward and reverse SDA and Bump primers designed to target the human BRCA1 gene, along with 100 ng HeLa genomic DNA, 0.32 U/µL Bst 2.0 DNA polymerase, and 0.2 U/µL BsoBI (New England Biolabs, Ipswich, Mass.) are added. A pH-sensitive dye is included at 100 mM.

What is claimed is:

1. A method for identifying a target nucleic acid in a sample comprising:
   (a) setting up a isothermal amplification reaction that comprises the sample, phenol red and 1.5 mM to 5 mM Tris or an equivalent thereof;
   (b) incubating the isothermal amplification reaction under isothermal amplification conditions; and, (c) after or during the incubation of (b), detecting by eye a change in color from red to yellow of the amplification reaction, wherein a color change of red to yellow indicates that the reaction comprises an amplification product.

2. The method of claim 1, wherein the amplification reaction is a loop-mediated isothermal amplification (LAMP) reaction.

3. The method of claim 1, wherein the amplification reaction is selected from a loop-mediated isothermal amplification (LAMP) reaction, a helicase dependent amplification (HDA) reaction, a strand displacement amplification (SDA) reaction, a recombinase polymerase amplification (RPA) reaction, a rolling circle amplification (RCA) reaction, a signal mediated amplification of RNA technology (SMART) reaction, a single primer isothermal amplification (SPIA) reaction, a nucleic acid sequence based amplification (NASBA) reaction and a nicking enzyme amplification reaction (NEAR) reaction.

4. The method according to claim 1, wherein the color change of (c) is compared to a control reaction in which no template has been added.

5. The method according claim 1, wherein the amplification has a starting pH in the range of pH 7-8.5.

6. The method according claim 1, wherein the amplification reaction comprises a biological sample.

7. The method according claim 1, wherein the method provides a diagnostic for infectious disease.

* * * * *